United States Patent
Mermelstein et al.

(10) Patent No.: US 6,893,648 B2
(45) Date of Patent: May 17, 2005

(54) COMPOSITION AND METHOD FOR TREATMENT OF VAGINAL DRYNESS

(76) Inventors: Harold Mermelstein, 3333 Henry Hudson Pkwy., Riverdale, NY (US) 10463; Frank P. Marchese, P.O. Box 1010, Bronxville, NY (US) 10708

( * ) Notice: Subject to any disclaimer, the term of this patent is extended or adjusted under 35 U.S.C. 154(b) by 0 days.

(21) Appl. No.: 10/037,526

(22) Filed: Jan. 4, 2002

(65) Prior Publication Data

US 2003/0170325 A1 Sep. 11, 2003

(51) Int. Cl.$^7$ .............................. A61K 6/00; A61K 7/00; A01N 25/00
(52) U.S. Cl. ........................ 424/401; 424/405; 424/484
(58) Field of Search ................................ 424/434, 436, 424/430, 431, 433

(56) References Cited

U.S. PATENT DOCUMENTS

| | | | |
|---|---|---|---|
| 6,242,012 B1 | * | 6/2001 | Newmark et al. .......... 424/756 |
| 2003/0045829 A1 | * | 3/2003 | Gehling et al. ................ 604/11 |
| 2003/0207971 A1 | * | 11/2003 | Stuart et al. ................. 524/274 |

OTHER PUBLICATIONS

Remington's Pharmaceutical Sciences, Eighteenth Edition, 1990, p. 1317.*

* cited by examiner

*Primary Examiner*—Thurman K. Page
*Assistant Examiner*—Sharon Howard

(57) ABSTRACT

Compositions in gel form or suppository are provided for treatment of vaginal dryness, wherein the composition comprises certain herbal compounds, with or without a vitamin such as, for example, vitamin A, C, D or E. The compositions may include an anti-bacterial agent and are applied to the affected area in an amount which is effective to provide the required relief when applied over a period of time.

31 Claims, No Drawings

COMPOSITION AND METHOD FOR TREATMENT OF VAGINAL DRYNESS

FIELD OF THE INVENTION

The present invention relates to a composition useful for treatment of vaginal dryness, pain and other problems arising from menopause and premenstrual symptoms, and is particularly related to such composition which contain specific combinations of natural substances such as herbs, in gel or suppository form. The present invention also relates to a method of preparation of such vaginal composition as well as their vaginal application to alleviate vaginal dryness, menopause and premenstrual symptoms.

BACKGROUND OF THE INVENTION

It is generally recognized that women at a certain age become afflicted with menopause and premenstrual symptoms which result in a variety of unpleasant problems, including vaginal dryness and pain. During menopause there is decrease in the hormone estrogen, or decrease in the hormone progesterone, a precursor to estrogen. Decreased estrogen levels can cause vaginal atrophy with the vaginal walls becoming drier and thinner. Women afflicted with these symptoms show less interest in sex due to pain during sexual intercourse, and at times exhibit slower arousal time. Such hormonal changes also disrupt the delicate acid-alkaline balance of the vagina which can lead to increased susceptibility to yeast and bacterial infections. U.S. Pat. No. 5,498,631 issued to Gorbach et al. on Mar. 12, 1996 discloses that symptoms of menopause can be treated by estrogen replacement therapy. However such treatment has been shown to increase the risk of certain cancers, such as endometrial cancer and breast cancer. As the aforementioned patent also discloses, changes in the level of endogenous estrogen may cause premenstrual syndrome in younger women. This condition is treated with a variety of non-hormonal therapies which can cause undesirable side effects. According to said patent, syndromes of menopause or premenstrual syndrome, or a condition which results from reduced levels of endogenous estrogen, may be prevented, or treated, by administering to the woman an effective amount of isoflavonoids, which are naturally occurring substances found primarily in soybeans. The isoflavonoids are administered by placing the patient on a diet containing high levels of soy-based foods such as, for example, tofu, miso, soybean or plant products rich in isoflavonoids.

Another patent, i.e., U.S. Pat. No. 5,612,061 issued to Simon W. Rabkin on Mar. 18, 1997 discloses a composition for the treatment of premenstrual syndrome comprising calcium, magnesium, acetaminophen and pamabrom, and a method of administering an effective amount of said composition to a patient in need of relief of premenstrual syndrome.

A more recent patent, i.e., U.S. Pat. No. 5,891,440 issued to Ephraim Philip Lansky on Apr. 6, 1999 discloses a phytoestrogen supplement which can be administered orally to relieve symptoms in menopausal women, or it can be administered topically as an ointment in order to relieve vaginal dryness and lack of skin tones. The ointment is prepared by pressing pomegranate seeds to obtain pomegranate seed oil, and mixing the seed oil with coconut milk to form the ointment. The ointment can also contain an ethanolic extract of Chinese asparagus root and shizandra berries.

Other investigators have addressed these uniquely female physiological problems and have developed oral medications which contain natural ingredients such as herbs and vitamins in order to provide relief from menopausal syndrome. However, none of the oral medications or other available medications has proven to be satisfactory for relieving vaginal dryness. Accordingly, there is a dire need for a composition, which can be conveniently applied to the vaginal area to provide the required relief from menopausal symptoms.

It is therefore an object of the present invention to provide a composition which is useful in providing a women with relief from vaginal dryness, premenstrual pain and menopausal symptoms.

It is another object of the present invention to provide such composition which contains certain combination of natural herbs for providing the required relief.

It is a further object of the present invention to provide said composition in gel form or a suppository which can be easily applied by the patient to the vaginal area in order to treat vaginal dryness, pain and other problems associated with menopause and premenstrual symptoms.

It is also an object of the present invention to provide a method of making said composition for topical application to the vaginal area.

The foregoing and other objects and features of the present invention will be more fully comprehended from the following detailed description, including clinical data obtained from topical application of the composition to women in need of relief from vaginal dryness and other menopausal problems.

SUMMARY OF THE INVENTION

The objects of the present invention are accomplished by providing compositions in gel form or a suppository. When used in gel form the composition comprises at least two herbal ingredients selected from any of the following herbs: aloe vera, evening primrose, red clover, dong quai, black cohosh, wild yam (Mexican and Chinese), chasteberry, cats claw, chamomile, calendula flowers, gingko biloba and green tea. In addition, the composition can also include olive oil and flax seed oil, and the olive oil may be replaced with cotton seed oil, sesame oil, jojoba oil, shark liver oil, vegetable oil (alone or with avocado), grapeseed oil, peanut oil, flax oil (unseeded), wheat germ oil or borage oil. Addition of vitamins such as vitamin E, A, C or D further enhances the effectiveness of the composition.

Compositions useful for treatment of vaginal dryness may also be made used in suppository form. These compositions also comprise at least two herbs, with or without vitamins, such as vitamin A, C, D or E, and other components.

The gel or suppository may be applied to the affected area by the person in need of relief.

DETAILED DESCRIPTION OF THE INVENTION

An effective composition for the purpose of this invention comprises at least two herbal ingredients. The two herbal ingredients may be selected from any of the following herbs: aloe Vera, evening primrose, red clover, dong quai, black cohosh, wild yam (Mexican and Chinese), chasteberry, cats claw, chamomile, calendula flowers, gingko biloba and green tea. In addition, the composition can include olive oil and flax seed oil, and the olive oil may be replaced with cotton seed oil, sesame oil, jojoba oil, shark liver oil, vegetable oil (alone or with avocado), grapeseed oil, peanut oil, flax oil (unseeded), wheat germ oil or borage oil.

Addition of vitamins such as vitamin E, A, C or D further enhances the effectiveness of the composition.

The composition of the present invention is used in gel form or as a suppository. When used in gel form it includes distilled water, propylene glycol (or glycerin) and a thickening agent, preferably sodium carboxymethyl cellulose (SCMC). Other thickening agents may be used in lieu of, or in combination with SCMC. These include pectin, algin and gum arabic.

The composition also includes an effective amount of anti-bacterial agent such as methyl paraben, propyl paraben and imidazolidinyl urea (germal 2), alone or in combination. Also, sufficient amount of citric acid is added to adjust the pH of the composition to about 5 to 6.5, preferably about 6.0.

A gel composition effective for treating vaginal dryness according to the present invention was prepared as follows:

1500 grams of distilled water was sterilized by heating to its boiling point and then allowed to cool to 30°. The distilled water was placed in a clean alcohol treated vessel equipped with a stirrer and 60 grams of SCMC (thickener) was slowly added to the distilled water with mild agitation. After completing the addition of SCMC, the mixture was allowed to stand for 24 hours until the thickener was completely hydrated. In a separate vessel, 3.0 grams of methyl paraben and 1.5 grams of propyl paraben were mixed with 32 grams of 100% propylene glycol. This mixture was then heated until all the parabens dissolved. The mixture was then allowed to cool to 45° C. and was thereafter added to the vessel containing the distilled water and the thickener, and the mixture was stirred mildly for 5 minutes followed by the addition of the following ingredients, successively, with continued stirring:

| Cats claw | 300 mg |
| --- | --- |
| Aloe vera | 360 mg |
| Gingko biloba | 105 mg |
| Evening primrose | 300 mg |
| Green tea | 315 mg |
| Chasteberry | 360 mg |
| Dong quai | 225 mg |
| Black cohosh | 210 mg |
| Wild yam | 870 mg |
| Olive oil | 6 gms |
| Vitamin E (300 I.U.) | 300 I.U. |
| Germal 2 | 1 gm |

The resulting mixture was stirred slowly for 2 hours, while adjusting its pH to 6.5 by adding citric acid. The product was a tan-colored gel having a viscosity of 60 centipoise at 25° C.

Forty-seven women were tested using the aforementioned composition. Of these, 39 had postmenopausal problems and 8 had premenstrual problems. The formulation was used as a gel on 39 postmenopausal women and was also used by the 8 premenstrual women. Each woman was instructed to apply the formulation twice daily for one week, using her fingers or an applicator. All patients were asked to evaluate the efficacy of the formulation, in providing relief, as follows:

Condition worsened
No change in condition
Fair improvement
Moderate improvement
Excellent improvement Of the 39 patients who had been suffering from vaginal dryness, 8 noted moderate improvement and 31 noted excellent improvement.

From the 30 patients who had painful intercourse experience, 2 indicated no change, 15 indicated that they had realized moderate improvement while the other 13 noted an excellent improvement.

Four of the 8 patients who suffered PMS reported moderate improvement and the other 4 indicated excellent improvement.

The herbs used in preparing the composition of this invention are themselves known in the art but, so far as it known, they have never been combined such as to form the composition of the present invention. A brief description of each herb used in the formulation of this invention is set forth below.

Dong Quai, is also known as Chinese Angelica, Dong Qua, Danqqui, Dang Gui, Tang Kuei, Tan Kue Bai Zhi. Its scientific name is Angelica Sinensis.

Red Clover, is also known as Cow Clover, Beebread, Meadow Clover, Purple Clover, Trefol, Trifolium, Wild Clover. Its scientific name is Trifolium Pratense from the family Leguminosae. It has been used topically for skin diseases. The applicable part of red clover is the flower top.

Black Cohosh, is also know as Black Snakeroot, Bugbane Bugwort, Cimicifuga, Squawroot, Rattle Root, Rattle Weed. Its scientific name is Cimicifuga Racemosa, from the family Ranunoulaceae. The applicable parts are the rhizome and root.

Chasteberry, this product is also known as Agnus Castos, Chaste Tree, Hemp Tree, Monk's Pepper. Its scientific name is Vitex Agnus Castus from the family Verbenacaea. Chasteberry has been used orally for the reduction of menopausal symptoms. Chasteberries are antiandrogenic.

Wild Yam, is also known as Mexican Yam, Wild Mexican Yam, Atlantic Yam, Barbasco, China Root, Colic Root, Devil's Bones, Rheumatism Root, Yuma. Its scientific names are Discorea Villosa, Discorea Floribunda, Discorea Composita, Discorea Mexicana, Discorea Macrostachya from the family Dioscoreaceae. The applicable part of Wild Yam is the root and rhizome. The tubers of the Dioscorea species contain the Glycoside Diosgenin which is a steroid precursor that has been used in the commercial production of estrogens and progestegens.

Green Tea, is also known as Chinese Tea. Its scientific names are Camellia Sinensis, Camellia Thea, Camellia Theifera, Thea Sinensis, Thea Bohea, Thea Viridis from the family Theaceae. The applicable parts are the leaf bud, leaf and stem.

Evening Primrose, is also known as Fever Plast, King's Cureall, Night Willow Herb, Scabish, Sundrop. Its scientific name is Oenothera Biennis from the family Onagraceae.

Aloe Vera Gel, is also known as Aloe, Aloe Gel, Aloe Vera, Aloe Leaf Gel, Aloe Copensis. Its scientific names are Aloe Vera, Aloe Barradensis, Aloe Ferrox, Aloe Africana, Aloe Spicata. Topically aloe gel is used for wound healing. Orally aloe vera gel is used as general tonic, anti-inflammatory agent and moisturizer.

Cats Claw, is also known as Una De Gato, Life Giving Vine of Peru, Samento. Its scientific name is Unacaria Tomentosa or Uncaria Guianensis. The scientific name for the family is Rubiaceae. Cats Claw is used orally for wound healing and as an anti-inflammatory agent. The applicable part of Cats Claw is the root and bark. It has the ability to dilate peripheral blood vessels.

Gingko Biloba, is also known as Maiden Hair, Tree, Kew Tree, Fossil Tree, Ginkyo, Yinhsing, Japanese Silver Apricot, Ginkgo Folium, Salisburia Adiantifolia, Bai Guoye, Bai Guo. Its scientific name is Ginkgo Biloba. The scientific family is Ginkgoacaea.

Vitamin E, is also known as Tocopherol, Alpha Tocopherol, D Alpha Tocopherol, DL Alpha Tocopherol. Its scientific name is Alpha Tocopherol. Orally Vitamin E is used for burn, inflammatory skin disorders, premenstrual syndrome and menopausal syndrome.

Flax Seed Oil, is also known as Flaxseed Oil and Linseed Oil. Its scientific name is Linum Usitatissimum of the family Linaceae.

Olive Leaf, is also known as Olivies and Oleae Folium. Its scientific name is Olea Europea of the family Oreaceae. Olive Leaf Extract is taken orally as an antiviral and antibacterial agent.

JoJoba Oil, is also known as Buxus Chinensis, a desert shrub. The oil is pressed from the seeds of the desert shrub. It is a liquid wax consisting almost entirely of esters of high molecular weight straight—chain monounsaturated alcohol and mono unsaturated acids (C18, C20, C22 and C24). This emollient is non-drying oil and is not prone to rancidity.

Borage Oil, is a European herb called Borago Officinalis. The oil is considered a demulcent providing a protective coating and has a soothing and softening effect on the skin.

As it was previously mentioned, any two of the herbal ingredients can form an effective composition for the purpose of this invention, when used with an oil such as olive oil, flaxseed oil or any of the other oils mentioned before, with or without vitamin E and mixed in distilled water, with added propylene glycol and an anti-bacterial agent, and thickened with SCMC or other equivalent thickening agent as aforesaid to form a smooth gel. The following compositions are effective for treatment of vaginal dryness. The bacterial agent used in each formulation was methyl paraben, propyl paraben and germal 2. The herbs were used as 1.5% solution in sterilized distilled water.

Composition #1

|  | % Wt. | Range % |
| --- | --- | --- |
| distilled water sterilized | 66 | 62 to 96 |
| SCMC | 5 | 1 to 10 |
| evening primrose 1.5% sol | 11.5 | 0.10 to 25 |
| dong quai 1.5% sol | 11 | 0.30 to 25 |
| vitamin E 175 IU | 0.01 | 0.01 to 0 |
| propylene glycol | 4.6 | 0 to 20 |
| olive oil | 1.5 | 0.01 to 15 |
| methyl paraben | 0.25 | 0.24 to 0.30 |
| propyl paraben | 0.12 | 0.12 to 0.15 |
| imidazolidinyl urea | 0.02 | 0.01 to 0.10 |
| TOTAL | 100 | |

Composition #2

|  | % Wt. | Range % |
| --- | --- | --- |
| distilled water sterilized | 66 | 62 to 96 |
| SCMC | 5 | 1 to 10 |
| evening primrose 1.5% sol | 11.5 | 0.10 to 25 |
| black cohash 1.5% | 11 | 0.30 to 25 |
| vitamin E 175 IU | 0.01 | 0.01 to 0 |
| propylene glycol | 4.6 | 0 to 20 |
| olive oil | 1.5 | 0.01 to 15 |
| methyl paraben | 0.25 | 0.24 to 0.30 |
| propyl paraben | 0.12 | 0.12 to 1.5 |
| imidazolidinyl urea | 0.02 | 0.01 to 0.10 |
| TOTAL | 100 | |

Composition #3

|  | % Wt. | Range % |
| --- | --- | --- |
| distilled water sterilized | 66 | 62 to 96 |
| SCMC | 5 | 1 to 10 |
| evening primrose 1.5% sol | 11.5 | 0.10 to 25 |
| chasteberry 1.5% sol | 11 | 0.30 to 25 |
| vitamin E 175 IU | 0.01 | 0.01 to 1 |
| propylene glycol | 4.6 | 0 to 20 |
| flaxseed oil | 1.5 | 0.01 to 15 |
| methyl paraben | 0.25 | 0.24 to 0.30 |
| propyl paraben | 0.12 | 0.12 to 1.5 |
| imidazolidinyl urea | 0.02 | 0.01 to 0.10 |
| TOTAL | 100 | |

Composition #4

|  | % Wt. | Range % |
| --- | --- | --- |
| distilled water sterilized | 66 | 62 to 96 |
| SCMC | 5 | 1 to 10 |
| evening primrose 1.5% sol | 11.5 | 0.10 to 25 |
| red clover 1.5% sol | 11 | 0.30 to 25 |
| vitamin E 150 IU | 0.01 | 0.01 to 1 |
| propylene glycol | 4.6 | 0 to 20 |
| flaxseed oil | 1.5 | 0.01 to 15 |
| methyl paraben | 0.25 | 0.24 to 0.30 |
| propyl paraben | 0.12 | 0.12 to 1.5 |
| imidazolidinyl urea | 0.02 | 0.01 to 0.10 |
| TOTAL | 100 | |

Composition #5

|  | % Wt. | Range % |
| --- | --- | --- |
| distilled water sterilized | 66 | 62 to 96 |
| SCMC | 5.0 | 1 to 10 |
| black cohosh | 11.5 | 0.10 to 25 |
| wild yam | 11.0 | 0.30 to 25 |
| vitamin E 300 IU | 0.01 | 0.01 to 1 |
| propylene glycol | 4.6 | 0 to 20 |
| flax seed oil | 1.5 | 0.01 to 15 |
| methyl paraben | 0.25 | 0.24 to 30 |
| propyl paraben | 0.12 | 0.12 to 1.5 |
| imidazolidinyl urea | 0.02 | 0.01 to 0.10 |
| TOTAL | 100 | |

Composition #6

|  | % Wt. | Range % |
|---|---|---|
| distilled water sterilized | 66 | 62 to 96 |
| SCMC | 5.0 | 1 to 10 |
| evening primrose | 11.50 | 0.10 to 25 |
| aloe vera gel | 11.0 | 0.30 to 25 |
| vitamin E 300 IU | 0.01 | 0.01 to 1 |
| propylene glycol | 4.6 | 0 to 20 |
| borage oil | 1.5 | 0.01 to 15 |
| methyl paraben | 0.25 | 0.24 to 0.30 |
| propyl paraben | 0.12 | 0.12 to 1.5 |
| imidazolidinyl urea | 0.02 | 0.01 to 0.10 |
| TOTAL | 100 | |

Composition #7

|  | % Wt. | Range % |
|---|---|---|
| distilled water sterilized | 66 | 62 to 96 |
| SCMC | 5 | 1 to 10 |
| dong quai 1.5% sol | 11.5 | 0.10 to 25 |
| aloe vera gel 1.5% sol | 11 | 0.30 to 25 |
| vitamin E 175 0IU | 0.01 | 0.01 to 1 |
| propylene glycol | 4.6 | 0 to 20 |
| borage oil | 1.5 | 0.01 to 15 |
| methyl paraben | 0.25 | 0.24 to 0.30 |
| propyl paraben | 0.12 | 0.12 to 0.15 |
| imidazolidinyl urea | 0.02 | 0.01 to 0.10 |
| TOTAL | 100 | |

Composition #8

|  | % Wt. | Range % |
|---|---|---|
| distilled water sterilized | 66 | 62 to 96 |
| SCMC | 5 | 1 to 10 |
| black cohosh 1.5% sol | 11.5 | 0.10 to 25 |
| aloe vera gel 1.5% sol | 11 | 0.30 to 25 |
| vitamin E 300 0IU | 0.01 | 0.01 to 1 |
| propylene glycol | 4.6 | 0 to 20 |
| borage oil | 1.5 | 0.01 to 15 |
| methyl paraben | 0.25 | 0.24 to 0.30 |
| propyl paraben | 0.12 | 0.12 to 0.15 |
| imidazolidinyl urea | 0.02 | 0.01 to 0.10 |
| TOTAL | 100 | |

Composition #9

|  | % Wt. | Range % |
|---|---|---|
| distilled water sterilized | 66 | 62 to 96 |
| SCMC | 5 | 1 to 10 |
| chasteberry 1.5% sol | 11.5 | 0.10 to 25 |
| aloe vera gel 1.5% sol | 11 | 0.30 to 25 |
| vitamin E 175 0IU | 0.01 | 0.01 to 1 |
| propylene glycol | 4.6 | 0 to 20 |
| borage oil | 1.5 | 0.01 to 15 |
| methyl paraben | 0.25 | 0.24 to 0.30 |
| propyl paraben | 0.12 | 0.12 to .15 |
| imidazolidinyl urea | 0.02 | 0.01 to 0.10 |
| TOTAL | 100 | |

Composition #10

|  | % Wt. | Range % |
|---|---|---|
| distilled water sterilized | 66 | 62 to 96 |
| SCMC | 5 | 1 to 10 |
| red clover 1.5% sol | 11.5 | 0.10 to 25 |
| aloe vera gel 1.5% sol | 11 | 0.30 to 10 |
| vitamin E 175 0IU | 0.01 | 0.01 to 1 |
| propylene glycol | 4.6 | 0 to 20 |
| olive oil | 1.5 | 0.01 to 15 |
| methyl paraben | 0.25 | 0.24 to 0.30 |
| propyl paraben | 0.12 | 0.12 to 0.15 |
| imidazolidinyl urea | 0.02 | 0.01 to 0.10 |
| TOTAL | 100 | |

Composition #11

|  | % Wt. | Range % |
|---|---|---|
| distilled water sterilized | 66 | 62 to 96 |
| SCMC | 5 | 1 to 10 |
| cats claw 1.5% sol | 11.5 | 0.10 to 25 |
| aloe vera gel 1.5% sol | 11 | 0.30 to 25 |
| vitamin E 175 IU | 0.01 | 0.01 to 1 |
| propylene glycol | 4.6 | 0 to 20 |
| borage oil | 1.5 | 0.01 to 15 |
| methyl paraben | 0.25 | 0.24 to 0.30 |
| propyl paraben | 0.12 | 0.12 to 0.15 |
| Imidazolidinyl urea | 0.02 | 0.01 to 0.10 |
| TOTAL | 100 | |

Composition #12

|  | % Wt. | Range % |
|---|---|---|
| distilled water sterilized | 66 | 62 to 96 |
| SCMC | 5 | 1 to 10 |
| cats claw 1.5% sol | 11.5 | 0.10 to 25 |
| red clover 1.5% sol | 11 | 0.30 to 25 |
| vitamin E 175 IU | 0.01 | 0.01 to 1 |
| propylene glycol | 4.6 | 0 to 20 |
| jojoba oil | 1.5 | 0.01 to 15 |
| methyl paraben | 0.25 | 0.24 to 0.30 |
| propyl paraben | 0.12 | 0.12 to 0.15 |
| imidazolidinyl urea | 0.02 | 0.01 to 0.10 |
| TOTAL | 100 | |

Composition #13

|  | % Wt. | Range % |
|---|---|---|
| distilled water sterilized | 66 | 62 to 96 |
| SCMC | 5 | 1 to 10 |
| cats claw 1.5% sol | 11.5 | 0.10 to 25 |
| chasteberry 1.5% sol | 11 | 0.30 to 25 |
| vitamin E 175 IU | 0.01 | 0.01 to 1 |
| propylene glycol | 4.6 | 0 to 20 |
| jojoba oil | 1.5 | 0.01 to 15 |
| methyl paraben | 0.25 | 0.24 to 0.30 |
| propyl paraben | 0.12 | 0.12 to 0.15 |
| imidazolidinyl urea | 0.02 | 0.01 to 0.10 |
| TOTAL | 100 | |

Composition #14

|  | % Wt. | Range % |
|---|---|---|
| distilled water sterilized | 66 | 62 to 96 |
| SCMC | 5 | 1 to 10 |
| evening primrose 1.5% sol | 11.5 | 0.10 to 25 |
| chamomile 1.5% sol | 11 | 0.30 to 25 |
| vitamin E 175 IU | 0.01 | 0.01 to 1 |
| propylene glycol | 4.6 | 0 to 20 |
| olive oil | 1.5 | 0.01 to 15 |
| methyl paraben | 0.25 | 0.24 to 0.30 |
| propyl paraben | 0.12 | 0.12 to 0.15 |
| imidazolidinyl urea | 0.02 | 0.01 to 0.10 |
| TOTAL | 100 | |

Composition #15

|  | % Wt. | Range % |
|---|---|---|
| distilled water sterilized | 66 | 62 to 96 |
| SCMC | 5 | 1 to 10 |
| black cohosh 1.5% sol | 11.5 | 0.10 to 25 |
| chamomile 1.5% sol | 11 | 0.30 to 10 |
| vitamin E 175 IU | 0.01 | 0.01 to 1 |
| propylene glycol | 4.6 | 0 to 20 |
| borage oil | 1.5 | 0.01 to 15 |
| methyl paraben | 0.25 | 0.24 to 0.30 |
| propyl paraben | 0.12 | 0.12 to 0.15 |
| imidazolidinyl urea | 0.02 | 0.01 to 0.10 |
| TOTAL | 100 | |

Composition #16

|  | % Wt. | Range % |
|---|---|---|
| distilled water sterilized | 66 | 62 to 96 |
| SCMC | 5 | 1 to 10 |
| dong quai 1.5% sol | 11.5 | 0.10 to 25 |
| chamomile 1.5% sol | 11 | 0.30 to 25 |
| vitamin E 175 IU | 0.01 | 0.01 to 1 |
| propylene glycol | 4.6 | 0 to 20 |
| olive oil | 1.5 | 0.01 to 15 |
| methyl paraben | 0.25 | 0.24 to 0.30 |
| propyl paraben | 0.12 | 0.12 to 0.15 |
| imidazolidinyl urea | 0.02 | 0.01 to 0.10 |
| TOTAL | 100 | |

Composition #17

|  | % Wt. | Range % |
|---|---|---|
| distilled water sterilized | 66 | 62 to 96 |
| SCMC | 5 | 1 to 10 |
| aloe vera gel 1.5% sol | 11.5 | 0.10 to 25 |
| chamomile 1.5% sol | 11 | 0.30 to 25 |
| vitamin E 175 IU | 0.01 | 0.01 to 1 |
| propylene glycol | 4.6 | 0 to 20 |
| jojoba oil | 1.5 | 0.01 to 15 |
| methyl paraben | 0.25 | 0.24 to 0.30 |
| propyl paraben | 0.12 | 0.12 to 0.15 |
| imidazolidinyl urea | 0.02 | 0.01 to 0.10 |
| TOTAL | 100 | |

Composition #18

|  | % Wt. | Range % |
|---|---|---|
| distilled water sterilized | 66 | 62 to 96 |
| SCMC | 5 | 1 to 10 |
| calendula 1.5% sol | 11.5 | 0.10 to 25 |
| aloe gel 1.5% sol | 0.01 | 0.30 to 25 |
| vitamin E 175 IU | 0.01 | 0.01 to 1 |
| propylene glycol | 4.6 | 0 to 20 |
| olive oil | 1.5 | 0.01 to 15 |
| methyl paraben | 0.25 | 0.24 to 0.30 |
| propyl paraben | 0.12 | 0.12 to 0.15 |
| imidazolidinyl urea | 0.02 | 0.01 to 0.10 |
| TOTAL | 100 | |

Composition #19

|  | % Wt. | Range % |
|---|---|---|
| distilled water sterilized | 66 | 62 to 96 |
| SCMC | 5 | 1 to 10 |
| dong quai 1.5% sol | 11.5 | 0.10 to 25 |
| black cohosh 1.5% sol | 11 | 0.30 to 25 |
| vitamin E 175 IU | 0.01 | 0.01 to 1 |
| propylene glycol | 4.6 | 0 to 20 |
| borage oil | 1.5 | 0.01 to 15 |
| methyl paraben | 0.25 | 0.24 to 0.30 |
| propyl paraben | 0.12 | 0.12 to 0.15 |
| imidazolidinyl urea | 0.02 | 0.01 to 0.10 |
| TOTAL | 100 | |

Composition #20

|  | % Wt. | Range % |
|---|---|---|
| distilled water sterilized | 66 | 62 to 96 |
| SCMC | 5 | 1 to 10 |
| dong quai 1.5% sol | 11.5 | 0.10 to 25 |
| chasteberry 1.5% sol | 11 | 0.30 to 25 |
| vitamin E 175 IU | 0.01 | 0.01 to 1 |
| propylene glycol | 4.6 | 0 to 20 |
| jojoba oil | 1.5 | 0.01 to 15 |
| methyl paraben | 0.25 | 0.24 to 0.30 |
| propyl paraben | 0.12 | 0.12 to 0.15 |
| imidazolidinyl urea | 0.02 | 0.01 to 0.10 |
| TOTAL | 100 | |

Composition #21

|  | % Wt. | Range % |
|---|---|---|
| distilled water sterilized | 66 | 62 to 96 |
| SCMC | 5 | 1 to 10 |
| dong quai 1.5% sol | 11.5 | 0.10 to 25 |
| chasteberry 1.5% sol | 11 | 0.30 to 25 |
| vitamin E 175 IU | 0.01 | 0.01 to 1 |
| propylene glycol | 4.6 | 0 to 20 |
| flax seed oil | 1.5 | 0.01 to 15 |
| methyl paraben | 0.25 | 0.24 to 0.30 |
| propyl paraben | 0.12 | 0.12 to 0.15 |
| imidazolidinyl urea | 0.02 | 0.01 to 0.10 |
| TOTAL | 100 | |

Composition #22

|  | % Wt. | Range % |
|---|---|---|
| distilled water sterilized | 66 | 62 to 96 |
| SCMC | 5 | 1 to 10 |
| dong quai 1.5% sol | 11.5 | 0.10 to 25 |
| wild yam 1.5% sol | 11 | 0.30 to 25 |
| vitamin E 175 IU | 0.01 | 0.01 to 1 |
| propylene glycol | 4.6 | 0 to 20 |
| jojoba oil | 1.5 | 0.01 to 15 |
| methyl paraben | 0.25 | 0.24 to 0.30 |
| propyl paraben | 0.12 | 0.12 to 0.15 |
| imidazolidinyl urea | 0.02 | 0.01 to 0.10 |
| TOTAL | 100 | |

Composition #23

|  | % Wt. | Range % |
|---|---|---|
| distilled water sterilized | 66 | 62 to 96 |
| SCMC | 5 | 1 to 10 |
| black cohosh 1.5% sol | 11.5 | 0.10 to 25 |
| chasteberry 1.5% sol | 11 | 0.30 to 25 |
| vitamin E 175 IU | 0.01 | 0.01 to 1 |
| propylene glycol | 4.6 | 0 to 20 |
| borage oil | 1.5 | 0.01 to 15 |
| methyl paraben | 0.25 | 0.24 to 0.30 |
| propyl paraben | 0.12 | 0.12 to 0.15 |
| imidazolidinyl urea | 0.02 | 0.01 to 0.10 |
| TOTAL | 100 | |

Composition #24

|  | % Wt. | Range % |
|---|---|---|
| distilled water sterilized | 66 | 62 to 96 |
| SCMC | 5 | 1 to 10 |
| chasteberry 1.5% sol | 11.5 | 0.10 to 25 |
| wild yam 1.5% sol | 11 | 0.30 to 25 |
| vitamin E 175 IU | 0.01 | 0.01 to 1 |
| propylene glycol | 4.6 | 0 to 20 |
| olive oil | 1.5 | 0.01 to 15 |
| methyl paraben | 0.25 | 0.24 to 0.30 |
| propyl paraben | 0.12 | 0.12 to 0.15 |
| imidazolidinyl urea | 0.02 | 0.01 to 0.10 |
| TOTAL | 100 | |

Composition #25

|  | % Wt. | Range % |
|---|---|---|
| distilled water sterilized | 66 | 62 to 96 |
| SCMC | 5 | 1 to 10 |
| dong quai 1.5% sol | 11.5 | 0.10 to 25 |
| red clover 1.5% sol | 11 | 0.30 to 25 |
| vitamin E 175 IU | 0.01 | 0.01 to 1 |
| propylene glycol | 4.6 | 0 to 20 |
| olive oil | 1.5 | 0.01 to 15 |
| methyl paraben | 0.25 | 0.24 to 0.30 |
| propyl paraben | 0.12 | 0.12 to 0.15 |
| imidazolidinyl urea | 0.02 | 0.01 to 0.10 |
| TOTAL | 100 | |

Composition #26

|  | % Wt. | Range % |
|---|---|---|
| distilled water sterilized | 66 | 62 to 96 |
| SCMC | 5 | 1 to 10 |
| dong quai 1.5% sol | 11.5 | 0.10 to 25 |
| cats claw 1.5% sol | 11 | 0.30 to 25 |
| vitamin E 175 IU | 0.01 | 0.01 to 1 |
| propylene glycol | 4.6 | 0 to 20 |
| olive oil | 1.5 | 0.01 to 15 |
| methyl paraben | 0.25 | 0.24 to 0.30 |
| propyl paraben | 0.12 | 0.12 to 0.15 |
| imidazolidinyl urea | 0.02 | 0.01 to 0.10 |
| TOTAL | 100 | |

Composition #27

|  | % Wt. | Range % |
|---|---|---|
| distilled water sterilized | 66 | 62 to 96 |
| SCMC | 5 | 1 to 10 |
| chasteberry 1.5% sol | 11.5 | 0.10 to 25 |
| red clover 1.5% sol | 11 | 0.30 to 25 |
| vitamin E 175 IU | 0.01 | 0.01 to 1 |
| propylene glycol | 4.6 | 0 to 20 |
| flax seed oil | 1.5 | 0.01 to 15 |
| methyl paraben | 0.25 | 0.24 to 0.30 |
| propyl paraben | 0.12 | 0.12 to 0.15 |
| imidazolidinyl urea | 0.02 | 0.01 to 0.10 |
| TOTAL | 100 | |

Composition #28

|  | % Wt. | Range % |
|---|---|---|
| distilled water sterilized | 66 | 62 to 96 |
| SCMC | 5 | 1 to 10 |
| red clover 1.5% sol | 11.5 | 0.10 to 25 |
| chamomile 1.5% sol | 11 | 0.30 to 25 |
| vitamin E 175 IU | 0.01 | 0.01 to 1 |
| propylene glycol | 4.6 | 0 to 20 |
| jojoba oil | 1.5 | 0.01 to 15 |
| methyl paraben | 0.25 | 0.24 to 0.30 |
| propyl paraben | 0.12 | 0.12 to 0.15 |
| imidazolidinyl urea | 0.02 | 0.01 to 0.10 |
| TOTAL | 100 | |

Composition #29

|  | % Wt. | Range % |
|---|---|---|
| distilled water sterilized | 66 | 62 to 96 |
| SCMC | 5 | 1 to 10 |
| chamomile 1.5% sol | 11.5 | 0.10 to 25 |
| calendula 1.5% sol | 11 | 0.30 to 25 |
| vitamin E 175 IU | 0.01 | 0.01 to 1 |
| propylene glycol | 4.6 | 0 to 20 |
| flax seed oil | 1.5 | 0.01 to 15 |
| methyl paraben | 0.25 | 0.24 to 0.30 |
| propyl paraben | 0.12 | 0.12 to 0.15 |
| imidazolidinyl urea | 0.02 | 0.01 to 0.10 |
| TOTAL | 100 | |

Composition #30

| | % Wt. | Range % |
|---|---|---|
| distilled water sterilized | 66 | 62 to 96 |
| SCMC | 5 | 1 to 10 |
| cats claw 1.5% sol | 11.5 | 0.10 to 25 |
| black cohosh 1.5% sol | 11 | 0.30 to 25 |
| vitamin E 175 IU | 0.01 | 0.01 to 1 |
| propylene glycol | 4.6 | 0 to 20 |
| jojoba oil | 1.5 | 0.01 to 15 |
| methyl paraben | 0.25 | 0.24 to 0.30 |
| propyl paraben | 0.12 | 0.12 to 0.15 |
| imidazolidinyl urea | 0.02 | 0.01 to 0.10 |
| TOTAL | 100 | |

Composition #31

| | % Wt. | Range % |
|---|---|---|
| distilled water sterilized | 66 | 62 to 96 |
| SCMC | 5 | 1 to 10 |
| cats claw 1.5% sol | 11.5 | 0.10 to 25 |
| chamomile 1.5% sol | 11 | 0.30 to 25 |
| vitamin E 175 IU | 0.01 | 0.01 to 1 |
| propylene glycol | 4.6 | 0 to 20 |
| olive oil | 1.5 | 0.01 to 15 |
| methyl araben | 0.25 | 0.24 to 0.30 |
| propyl paraben | 0.12 | 0.12 to 0.15 |
| imidazolidinyl urea | 0.02 | 0.01 to 0.10 |
| TOTAL | 100 | |

Composition #32

| | % Wt. | Range % |
|---|---|---|
| distilled water sterilized | 66 | 62 to 96 |
| SCMC | 5 | 1 to 10 |
| chasteberry 1.5% sol | 11.5 | 0.10 to 25 |
| wild yam 1.5% sol | 11 | 0.30 to 25 |
| vitamin E 175 IU | 0.01 | 0.01 to 1 |
| propylene glycol | 4.6 | 0 to 20 |
| olive oil | 1.5 | 0.01 to 15 |
| methyl paraben | 0.25 | 0.24 to 0.30 |
| propyl paraben | 0.12 | 0.12 to 0.15 |
| imidazolidinyl urea | 0.02 | 0.01 to 0.10 |
| TOTAL | 100 | |

Composition #33

| | % Wt. | Range % |
|---|---|---|
| distilled water sterilized | 66 | 62 to 96 |
| SCMC | 5 | 1 to 10 |
| cats claw 1.5% sol | 11.5 | 0.10 to 25 |
| evening primrose 1.5% sol | 11 | 0.30 to 25 |
| vitamin E 175 IU | 0.01 | 0.01 to 1 |
| propylene glycol | 4.6 | 0 to 20 |
| olive oil | 1.5 | 0.01 to 15 |
| methyl paraben | 0.25 | 0.24 to 0.30 |
| propyl paraben | 0.12 | 0.12 to 0.15 |
| imidazolidinyl urea | 0.02 | 0.01 to 0.10 |
| TOTAL | 100 | |

Composition #34

| | % Wt. | Range % |
|---|---|---|
| distilled water sterilized | 66 | 62 to 96 |
| SCMC | 5 | 1 to 10 |
| cats claw 1.5% sol | 11.5 | 0.10 to 25 |
| chamomile 1.5% sol | 11 | 0.30 to 25 |
| vitamin E 175 IU | 0.01 | 0.01 to 1 |
| propylene glycol | 4.6 | 0 to 20 |
| olive oil | 1.5 | 0.01 to 15 |
| methyl paraben | 0.25 | 0.24 to 0.30 |
| propyl paraben | 0.12 | 0.12 to 0.15 |
| imidazolidinyl urea | 0.02 | 0.01 to 0.10 |
| TOTAL | 100 | |

Composition #35

| | % Wt. | Range % |
|---|---|---|
| distilled water sterilized | 66 | 62 to 96 |
| SCMC | 5 | 1 to 10 |
| green tea 1.5% sol | 11.5 | 0.10 to 25 |
| calendula 1.5% sol | 11 | 0.30 to 25 |
| vitamin E 175 IU | 0.01 | 0.01 to 1 |
| propylene glycol | 4.6 | 0 to 20 |
| olive oil | 1.5 | 0.01 to 15 |
| methyl paraben | 0.25 | 0.24 to 0.30 |
| propyl paraben | 0.12 | 0.12 to 0.15 |
| imidazolidinyl urea | 0.02 | 0.01 to 0.10 |
| TOTAL | 100 | |

Composition #36

| | % Wt. | Range % |
|---|---|---|
| distilled water sterilized | 66 | 62 to 96 |
| SCMC | 5 | 1 to 10 |
| green tea 1.5% sol | 11.5 | 0.10 to 25 |
| evening primrose 1.5% sol | 11 | 0.30 to 25 |
| vitamin E 175 IU | 0.01 | 0.01 to 1 |
| propylene glycol | 4.6 | 0 to 20 |
| olive oil | 1.5 | 0.01 to 15 |
| methyl paraben | 0.25 | 0.24 to 0.30 |
| propyl paraben | 0.12 | 0.12 to 0.15 |
| imidazolidinyl urea | 0.02 | 0.01 to 0.10 |
| TOTAL | 100 | |

Composition #37

| | % Wt. | Range % |
|---|---|---|
| distilled water sterilized | 66 | 62 to 96 |
| SCMC | 5 | 1 to 10 |
| green tea 1.5% sol | 11.5 | 0.10 to 25 |
| chamomile 1.5% sol | 11 | 0.30 to 25 |
| vitamin E 175 IU | 0.01 | 0.01 to 1 |
| propylene glycol | 4.6 | 0 to 20 |
| olive oil | 1.5 | 0.01 to 15 |
| methyl paraben | 0.25 | 0.24 to 0.30 |
| propyl paraben | 0.12 | 0.12 to 0.15 |
| imidazolidinyl urea | 0.02 | 0.01 to 0.10 |
| TOTAL | 100 | |

| Composition #38 | | |
|---|---|---|
| | % Wt. | Range % |
| distilled water sterilized | 66 | 62 to 96 |
| SCMC | 5 | 1 to 10 |
| green tea 1.5% sol | 11.5 | 0.10 to 25 |
| wild yam 1.5% sol | 11 | 0.30 to 25 |
| vitamin E 175 IU | 0.01 | 0.01 to 1 |
| propylene glycol | 4.6 | 0 to 20 |
| olive oil | 1.5 | 0.01 to 15 |
| methyl paraben | 0.25 | 0.24 to 0.30 |
| propyl paraben | 0.12 | 0.12 to 0.15 |
| imidazolidinyl urea | 0.02 | 0.01 to 0.10 |
| TOTAL | 100 | |

Compositions useful for treatment of vaginal dryness may also be used in suppository form. The following are examples of suppository compositions which are useful for this purpose. In these composition Polymol (wax) is used instead of distilled water. Polymol wax is a mixture of 43.4 weight % polyglycerin-6 octylmyristate, 14.4 weight % polyglyceryl-6 octahydroxystearate and 19.1 weight % pharmaceutical grade cocoa butter. The mixture is heated to 48° C. on steam bath followed by the addition of the remaining ingredients with continuous stirring to obtain a uniform mixture. This mixture was poured into a mold and cooled. A two gram suppository was formed (60 total) and given to patients to evaluate as a moisturizer. Two exemplary compositions are as follows:

| Composition #39 | | |
|---|---|---|
| | % Wt. | Range % |
| polyglycerin -6 octylmyristate | 43.4 | 40 to 75 |
| polyglyceryl -6 octahydroxystearate | 14.4 | 10 to 25 |
| cocoa butter (pharmaceutical grade) | 19.1 | 50 |
| evening primrose 1.5% sol | 4.6 | 0.10 to 25 |
| chamomile 1.5% sol | 4.2 | 0.30 to 25 |
| vitamin E 175 IU | 0.2 | 0.01 to 1 |
| propylene glycol | 11.5 | 0 to 20 |
| olive oil | 2 | 0.01 to 15 |
| methyl paraben | 0.3 | 0.24 to 0.30 |
| propyl paraben | 0.15 | 0.12 to 0.15 |
| imidazolidinyl urea | 0.15 | 0.01 to 0.10 |
| TOTAL | 100 | |

| Composition #40 | | |
|---|---|---|
| | % Wt. | Range % |
| polyglycerin -6 octylmyristate | 43.4 | 40 to 75 |
| polyglyceryl -6 octahydroxystearate | 14.4 | 10 to 25 |
| cocoa butter (pharmaceutical grade) | 19.1 | 10 to 50 |
| dong quai 1.5% sol | 4.6 | 0.10 to 25 |
| chasteberry 1.5% sol | 4.2 | 0.30 to 25 |
| vitamin E 175 IU | 0.2 | 0.01 to 1 |
| propylene glycol | 11.5 | 0 to 20 |
| olive oil | 2 | 0.01 to 15 |
| methyl paraben | 0.3 | 0.24 to 0.30 |
| propyl paraben | 0.15 | 0.12 to 0.15 |
| imidazolidinyl urea | 0.15 | 0.01 to 0.10 |
| TOTAL | 100 | |

Although only two suppository compositions have been illustrated with specific herbs-vitamin E combinations, other herb combinations may be used in preparing the formulations, with or without vitamin E, such as those described for the gel compositions in Examples 1–39. Other vitamins such as vitamin A, C or D may be substituted for vitamin E, or may be used in combination therewith. Also, the wax in the formulation may be replaced with polyoxyethylene glycol having molecular weight between about 400 and about 6000. In addition, polyoxyethylene glycol may be combined with other thickeners such as gum guar or pectin, algin or SCMC.

What is claimed is:

1. A therapeutic composition for treatment of vaginal dryness comprising an effective amount of at least two herbal compounds selected from the group consisting of: aloe vera, evening primrose, red dover, dong quai, black cohosh, wild yam, chasteberry, cat's claw, chamomile, calendula flower, gingko biloba, and green tea, said two herbal compounds used in combination with olive oil, flax seed oil or unseeded flax oil, jojoba oil, borage oil, distilled water, propylene glycol and an effective amount of thickening agent to make said composition in gel form.

2. A therapeutic composition as in claim 1 further including an effective amount of anti-bacterial agent.

3. A therapeutic composition as in claim 2 wherein said anti-bacterial agent is selected from the group consisting of methyl paraben, propyl paraben, imidazolidinyl urea and mixtures thereof.

4. A therapeutic composition as in claim 1 wherein said herbal compounds are evening primrose and chasteberry used in combination with jojoba oil and borage oil.

5. A therapeutic composition as in claim 4 further including an effective amount of anti-bacterial agent.

6. A therapeutic composition as in claim 5 wherein said anti-bacterial agent is selected from the group consisting of methyl paraben, propyl paraben, imidazolidinyl urea and mixtures thereof.

7. A therapeutic composition as in claim 1 wherein said herbal compounds are dong quai and chasteberry used in combination with jojoba oil and borage oil.

8. A therapeutic composition as in claim 7 further including an effective amount of anti-bacterial agent.

9. A therapeutic composition as in claim 8 wherein said anti-bacterial agent is selected from the group consisting of methyl paraben, propyl paraben, imidazolidinyl urea and mixtures thereof.

10. A therapeutic composition as in claim 1 wherein said herbal compounds are evening primrose and dong quai used in combination with jojoba oil and borage oil.

11. A therapeutic composition as in claim 10 including an effective amount of anti-bacterial agent.

12. A therapeutic composition as in claim 11 wherein said anti-bacterial agent is selected from the group consisting of methyl paraben, propyl paraben, imidazolidinyl urea and mixtures thereof.

13. A method for treatment of vaginal dryness comprising administering to a person in need of such treatment an effective amount of a therapeutic composition defined by claim 1.

14. A method for treatment of vaginal dryness comprising administering to a person in need of such treatment an effective amount of a therapeutic composition defined by claim 2.

15. A method for treatment of vaginal dryness comprising administering to a person in need of such treatment an effective amount of a therapeutic composition defined by claim 3.

16. A therapeutic composition in suppository form, for treatment of vaginal dryness, comprising an effective amount of at least two herbal compounds selected from the group consisting of aloe vera, evening primrose, red clover, dong quai, black cohosh, wild yam, chasteberry, cat's claw, chamomile, calendula flower, gingko biloba and green tea, said two herbal compounds used in combination with olive oil, jojoba oil, borage oil, propylene glycol and a wax selected from the group consisting of polyglycerin-6 octylmyristate, polyglyceryl-6 octahydroxystearate, cocoa butter and mixtures thereof.

17. A therapeutic composition as in claim 16 further including an effective amount of anti-bacterial agent.

18. A therapeutic composition as in claim 17 wherein said anti-bacterial agent is selected from the group consisting of methyl paraben, propylparaben, imidazolidinyl urea and mixtures thereof.

19. A therapeutic composition as in claim 16 wherein said herbal compounds are dong quai and chasteberry used in combination with jojoba oil and borage oil.

20. A therapeutic composition as in claim 19 further including an effective amount of anti-bacterial agent.

21. A therapeutic composition as in claim 20 wherein said anti-bacterial agent is selected from the group consisting of methyl paraben, propyl paraben, imidazolidinyl urea and mixtures thereof.

22. A therapeutic composition as in claim 16 wherein said herbal compounds are evening primrose and chamomile used in combination with jojoba oil and borage oil.

23. A therapeutic composition as in claim 21 further including an effective amount of anti-bacterial agent.

24. A therapeutic composition as in claim 21 wherein said anti-bacterial agent is selected from the group consisting of methyl paraben, propyl paraben, imidazolidinyl urea and mixtures thereof.

25. A method for treatment of vaginal dryness comprising administering to a person in need of such treatment an effective amount of a therapeutic composition defined by claim 16.

26. A method for treatment of vaginal dryness comprising administering to a person in need of such treatment an effective amount of a therapeutic composition defined by claim 17.

27. A method for treatment of vaginal dryness comprising administering to a person in need of such treatment an effective amount of a therapeutic composition defined by claim 18.

28. A therapeutic composition, in suppository form, for treatment of vaginal dryness, comprising an effective amount of at least two herbal compounds selected from the group consisting of aloe vera, evening primrose, red clover, dong quai, black cohosh, wild yam, chasteberry, cat's claw, chamomile, calendula flower, gingko biloba and green tea, said two herbal compounds used in combination with olive oil, jojoba oil, borage oil, propylene glycol and a polyoxyethyleneglycol having a molecular weight between about 400 and 600.

29. A therapeutic composition as in claim 28 further including an effective amount of anti-bacterial agent.

30. A therapeutic composition as in claim 29 wherein said anti-bacterial agent is selected from the group consisting of methyl paraben, propylparaben, imidazolidinyl urea and mixtures thereof.

31. A method for treatment of vaginal dryness comprising administering to a person in need of such treatment an effective amount of a therapeutic composition defined by claim 28.

* * * * *